United States Patent [19]

Stimac

[11] Patent Number: 4,925,663

[45] Date of Patent: May 15, 1990

[54] BIOLOGICAL CONTROL OF IMPORTED FIRE ANTS WITH A FUNGAL PATHOGEN

[75] Inventor: Jerry L. Stimac, Gainesville, Fla.

[73] Assignee: University of FLorida, Gainesville, Fla.

[21] Appl. No.: 140,018

[22] Filed: Dec. 31, 1987

[51] Int. Cl.$^5$ .............................................. C12N 1/14
[52] U.S. Cl. ........................................ 424/93; 424/92; 435/254; 435/911
[58] Field of Search .................... 424/92, 93; 435/911, 435/254

[56] References Cited

U.S. PATENT DOCUMENTS 4,751,082 6/1988 Schaerffenberg et al. ............ 424/93

OTHER PUBLICATIONS

Chem-Abstracts, vol. 72, 1970, 89237q, Sukhov.
Chem-Abstracts, vol. 73, 1970, 13464m, Velitskaya.
Chem-Abstracts, vol. 100, 1984, 116441g, Anderson et al.
Chem-Abstracts, vol. 70, 1969, 46398j, Brikman et al.
Chem-Abstracts, vol. 86, 1977, 84761k, Schaerffenberg et al.

*Primary Examiner*—Howard E. Schain
*Attorney, Agent, or Firm*—Saliwanchik & Saliwanchik

[57] ABSTRACT

The subject invention concerns a novel biopesticide and its use to control imported fire ants which have caused significant economic harm to much of the southeastern United States. Specifically, a highly virulent isolate of *Beauveria bassiana* in an agricultural composition, can be used to effectively control ants of the genus *Solenopsis*. Exemplified herein is *Beauveria bassiana* No. 447, ATCC 20872. By using this novel fungus, or mutants thereof, fire ants can be controlled without the environmental and public safety hazards presented by chemical control agents.

13 Claims, No Drawings

BIOLOGICAL CONTROL OF IMPORTED FIRE ANTS WITH A FUNGAL PATHOGEN

BACKGROUND OF THE INVENTION

The imported fire ants (IFA), *Solenopsis invicta* and *Solenopsis richteri* were introduced into the United States in the early 1900's at the port of Mobile, Ala. By the late 1940's and early 1950's these fire ants, particularly *S. invicta*, were present at nurseries from Miami, Fla. to San Antonio, Tex. and as far north as North Carolina. Imported fire ants displace the native ant fauna and, in many areas of the southeastern United States, have become the dominant ant species. IFA have colonized a wide range of habitats and have proven to be particularly successful at colonizing disturbed lands such as cultivated farmland. Currently, the imported fire ants infest 230 million acres in the southern United States, including all 67 counties in Florida. *Solenopsis invicta* is the species responsible for over 95% of the infestation in the United States.

The imported fire ant has gained notoriety primarily as a result of its painful sting and its inclination to feed on a wide array of materials, including cultivated plants and underground wires. The fire ant sting is not only painful but is potentially life threatening for people who suffer from an allergic reaction to the sting.

Fire ants live in nests in the ground, therefore, they are a particular nuisance in schoolyards, recreational areas, and homeowners' yards. Although the nests are often underground, they may reach 1 to 2 feet in height above the ground. These mounds are especially troublesome for homeowners because they present a hazard for children and pets, in addition to being unsightly.

Farmers throughout the southern states have suffered large economical losses as the result of fire ant infestations. Fire ants reduce the active foraging area in pastures because animals do not forage well around fire ant nests. Fire ants may also damage plants by chewing on stems or fruits. IFA has been reported to cause serious damage in young citrus groves and in vegetable crops with high cash values. Also, these ants make it difficult to harvest some crops such as hay and citrus. Large fire ant mounds may also cause damage to agricultural equipment especially in heavy clay soil areas.

Additional economic loss has resulted from the IFA chewing on electrical wiring and telephone lines in the ground or even housed in containers above the ground.

In response to the then serious economic and public safety threat, well over $200 million was spent by the state and federal governments between 1950 and 1982 in efforts to control or eradicate these ants. Additional funds have also been provided by local agencies, as well as private citizens. Despite this tremendous commitment of resources in an attempt to control these pests, IFA have spread, largely unchecked, through the southeastern United States.

Control efforts to date have focused on the identification of chemical control agents. Unfortunately, the use of chemical control agents has been largely ineffective and can, in fact, lead to increased populations of IFA. This increase occurs in the following way: broadcast application of non-specific formicides results in the temporary control of all ant species; then, IFA reinfests the area faster than native ant species. The net result is an inadvertent increase in IFA populations, allowing IFA to become the dominant species more quickly than if no control action were taken. IFA nest densities can increase more than 30-fold within 1 to 2 years following broadcast chemical treatment of an area where IFA densities are initially low.

In addition to being ineffective in the battle to control IFA, chemical control agents present the usual hazards associated with the use of chemical pesticides. These hazards include the poisoning of soil and underlying aquifiers; pollution of surface waters as a result of runoff; and the destruction of non-target life forms.

Chemical control agents have the further disadvantage of presenting public safety hazards when they are applied in areas where pets, farm animals, or children may come in contact with them. This makes chemical agents particularly disadvantageous for the control of IFA in school yards, pasture lands, and residential areas.

Because of the ineffectiveness of chemical control agents, as well as, the many health and environmental problems associated with their use, increasing research attention has turned toward the development of biological control agents. Unfortunately the search for biological control agents has been largely unfruitful. No predators, parasites, or pathogens indigenous to the United States have proven to be effective biological controls of IFA, although some native ant species may retard IFA colonization in areas that are not frequently or severely disturbed.

BRIEF SUMMARY OF THE INVENTION

The subject invention concerns the use of highly virulent Beauveria bassiana to control imported fire ants (IFA). Specifically exemplified herein is *B. bassiana* isolate No. 447. This fungus, advantageously, shows unexpectedly high virulence against IFA and does not produce the environmental hazards associated with chemical control agents. The fungus can be applied to IFA nests in lawns, school yards, pastures, nurseries, and anywhere that fire ants are a problem. The subject invention also includes mutants of *B. bassiana* No. 447 which substantially retain the high virulence to Solenopsis species of the parent strain.

DETAILED DESCRIPTION OF THE INVENTION

A biologically pure culture of a novel isolate of *Beauveria bassiana* of the subject invention, No. 447, has been deposited in the American Type Culture Collection (ATCC), 12301 Parklawn Drive, Rockville, MD 20852.

| Culture | Accession number | Deposit Date |
| --- | --- | --- |
| *Beauveria bassiana* No. 447 | ATCC 20872 | Dec. 29, 1987 |

The subject culture has been deposited under conditions that assure that access to the culture will be available during the pendency of the patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

The entomapathogenic fungus *Beauveria bassiana* is an imperfect fungus (Fungi Imperfecti) in the subdivision Deuteromycotonia. The genus Beauveria Vuill is within the Class Deuteromycetes and is distinguished from other genera by having conidia that are borne singly, not catenulate and having the fertile portion of the conidiophore zig-zag in shape and drawn out at the tip. The species *Beauveria bassiana* has spherical not ellipsoid conidia measuring 2-3 micrometers by 2-2.5 micrometers and with conidiophores forming dense bunches. The novel isolate of *B. bassiana* is the first known fungus of this species which is highly virulent to IFA. For a biological control agent to be effective at a practical level to control IFA, it is essential that the agent not only exhibit pathogenicity against IFA, but it must also be virulent. The more virulent it is, the better it is an a biocontrol agent. Though some *B. bassiana* isolates have been shown to have some pathogenicity to IFA, these isolates did not have the essential virulence to function as a biocontrol agent. There is no known way to convert a pathogenic non-virulent *B. bassiana* isolate into a pathogenic virulent *B. bassiana*. Thus, the discovery of the novel isolate of the invention accomplishes a goal which has long been sought after.

MODE OF ACTION AND VIRULENCE

Like most entomogenous fungi, *Beauveria bassiana* initiates infection by a germinating spore (conidium) attaching to and subsequently penetrating the cuticle of the insect host. Advantageously, and unexpectedly, the claimed *Beauveria bassiana* attaches very securely to the cuticle of IFA and is typically not removed by the ant's grooming activities. This may account somewhat for the high virulence of the fungus. As the fungus penetrates the ant's cuticle, the invasive hyphae begin to enter the host's tissues and ramify through the hemocoel. Hyphal bodies or segments of the hyphae distribute throughout the hemocoel, filling the dying insect with mycelium. Emergence hyphae grow out through the insect's integument and produce spores on the external surface of the host. These spores, or conidia, are dispersed and capable of infecting new host insects.

With the fire ant host, *B. bassiana* spores are dispersed within the nest by the activities of worker ants and the queen is infected by contact with infected workers, soil, or food material. After the queen is infected and dies, the fire ant colony cannot produce uninfected workers so the colony eventually dies off completely.

Experiments with the novel isolate, *B. bassiana* No. 447, have shown that the fungus of the subject invention is highly virulent against the target pest--fire ants of the genus Solenopsis. In assessing the virulence of a fungal control agent four factors are evaluated:

1. The proportion of kill of each of the life stages of the fire ant: eggs. larvae, pupae, adult workers and queen.
2. How fast the kill is.
3. What proportion of individuals killed can produce viable spores which can re-infect.
4. How many spores capable of re-infecting are produced by individual infected ants.

The novel isolate of the invention shows exceptionally good results for each of these four factors. The isolate is, advantageously, highly virulent against all life stages of the IFA. Of particular significance is the fungus' ability to kill the queen. The queen is the only ant capable of producing eggs. Once the queen is destroyed, the entire colony will inevitably die out except on rare occasions when another virgin queen is accepted. The demise of the rest of the colony is expedited by the fungus' ability to kill workers and the immature stages of the ants as well.

The fungus works rapidly; a remarkable 90 to 100% kill of all life stages occurs within 3 to 10 days of application. Significantly, more than 70% of the kill occurs within one week of application. Spore concentrations of from about $1 \times 10^7$ to about $1 \times 10^{10}$ per ml or gm of carrier can be used.

Following are examples which illustrate the process of the invention, including the best mode. These examples should not be construed as limiting. All solvent mixture proportions are by volume unless otherwise noted.

EXAMPLE 1

PREPARATION OF THE FUNGUS

The subject fungus can be produced in trays with a rice-based medium. An isolate of fungal inoculum is used to initiate the growth of the fungus in the trays.

The initial inoculum is prepared in petri dishes. The pure spores are then transferred into jars containing sterile white rice without skins.

The medium for the trays is prepared by:
1. The rice is pre-cooked for 10 minutes.
2. 750 grams of cooked rice is placed in polyethylene bags and sterilized in an autoclave at 120° C. for 30 minutes.
3. Within a laminar flow hood, one teaspoon of spores and rice from the inoculum jars is added to each bag of prepared sterile medium.
4. Each bag is closed tightly by folding and stapling the open end.
5. The bags are transferred to a sterile room with positive pressure, temperature at 25.0 to 27.0° C., relative humidity above 70%, and 16 hours photophase. This room is known as the "environment room."

After 3 days in the environment room, bags containing mycelia are selected and their contents are transferred to plastic trays. The size of the trays is such that each tray will accommodate the contents of 2 to 3 bags. The trays and their contents are left in the environment room for 12 to 15 days. At the end of the 12 to 15 day period, the trays are transferred to a room with a cool (10 to 20° C.) current of clean air. The trays are left in this room until the cool air has dried the rice and fungus mixture.

The uncontaminated trays of rice covered with fungus can be harvested and prepared for application or storage. If the fungus will be applied to fire ants nests within 1 to 2 weeks after production, the contents of the trays can be collected with sterile spatulas and placed into sterile plastic bags or the rice particles can be ground slowly into small particles and then placed into plastic bags. The resulting product contains spores, mycelia, and small pieces of rice.

If the fungus is to be stored, the ground spore/small-particle mixture can be mixed with talc and placed into sterile plastic containers sealed tightly and stored out of direct sunlight in a room with a temperature range of 10°–25° C. The high virulence of the *B. bassiana* can be compromised by bacterial or fungal contamination. Therefore, throughout the preparation of the fungus, great care must be taken to maintain the sterility of all instruments and equipment.

APPLICATION OF FUNGUS TO TARGET FIRE ANTS

As the following examples demonstrate, the fungus-containing product can be applied to fire ants and their nests as a liquid, powder, or put out as a bait for the ants to forage and bring back to the nest.

EXAMPLE 2

SPRAY OR DRENCH APPLICATION

Spraying is most effective for treating individual ants or small groups of ants. A fungal suspension containing $1.0 \times 10^7$ to $1.0 \times 10^9$ spores per milliliter of water and 2 drops of TWEEN$^{TM}$ per liter was sprayed on laboratory ants using an airbrush as an applicator. The TWEEN$^{TM}$ acts as a wetting agent and other equivalent wetting agents could be used. Groups of 10 ants were sprayed for 1 to 2 seconds at 15 psi. The fungal spray applied in this manner infected and killed 90 to 100% of all life stages of *Solenopsis invicta* within 3 to 10 days.

For fire ant nests in the soil, a drench method can be used. To each nest, 1 liter of the fungal suspension described above can be applied by slowly pouring the liquid over the top of the nest and allowing it to filter down through the nest tunnels. This method is most effective when it is not raining and when the ambient temperatures are between 5° and 35° C.

EXAMPLE 3

POWDER APPLICATION

A ground rice, fungal spore, and mycelia mixture can be applied to fire ant nests in soil as a dry powder.

The powder is prepared as directed in Example 1 above. The rice covered with *B. bassiana* is slowly ground into a powder which contains the rice, spores, and mycelium. Application of this powder to the fire ant nests is the preferred method of practicing the invention because the presence of both the spores and the mycelium facilitates rapid and widespread fungal growth within the nest.

The application can be accomplished using an aerosol applicator with an attachment that distributes the mixture in the tunnels below the soil surface and within the nest. The applicator is placed over the nest and the powder is pumped into the nest until it is distributed well through the tunnels. Care should be taken to place the attachment distributors under the soil surface so that spores are forced into the subsurface tunnels rather than becoming airborne. During and following application, ants covered with white powder will be observed. These infected ants will die within 1 to 5 days and the spores they produce will be infective to other fire ants. The colony should decrease activity within 1 to 3 days and die within 2 weeks following application. Active spores will remain in the soil at the nest site thereby discouraging the return of IFA.

EXAMPLE 4

BAIT APPLICATION

Rice particles covered with fungus may be used as a bait which will be foraged by fire ants and carried down into the nest, thereby introducing spores of the fungal disease into the nest. Vegetable oil may be added to the rice/fungal mixture to make the bait more attractive to the ants. Initially the bait should be sprinkled around the outer edges of the raised nest. Then disturb the nest by gently scraping away the soil from the top of the nest. Finally, the mixture of particles and fungal spores should be sprinkled over the top of the open nest. A quantity of 50 to 200 grams of bait should be applied to each nest, depending upon the nest size.

I claim:

1. A *Beauveria bassiana* which, when in its essentially biologically pure form, has the virulence against fire ants characteristic of *Beauveria bassiana* No. 447 culture deposit ATCC 2087, and mutants thereof.

2. A composition for controlling imported fire ants comprising *Beauveria bassiana*, wherein said *Beauveria bassiana* has the virulence against fire ants characteristic of *Beauveria bassiana* No. 447, culture deposit ATCC 20872, in association with an agricultural carrier.

3. A composition, according to claim 2, wherein the agricultural carrier is a liquid, a powder, granules, or small particles.

4. A composition, according to claim 3, wherein the liquid comprises water and a wetting agent.

5. A composition, according to claim 2, wherein the agricultural carrier comprises rice or ground-up rice.

6. A composition, according to claim 2, wherein said agricultural carrier is a liquid and said *Beauveria bassiana* is in the spore form at a spore concentration of from about $1 \times 10^7$ spores/ml of carrier to about $1 \times 10^{10}$ spores/ml of carrier.

7. A composition, according to claim 2, wherein the agricultural carrier is rice and said fungus is present in the form of spores and/or mycelia.

8. A process for controlling imported fire ants of the genus Solenopsis which comprises applying a *Beauveria bassiana*, wherein said *Beauveria bassiana* has the virulence against fire ants characteristic of *Beauveria bassiana* No. 447, culture deposit ATCC 20872, onto said fire ants, or their surroundings.

9. A process, according to claim 8, wherein said fungus and a liquid carrier is applied directly to individual ants or small groups of ants.

10. A process, according to claim 8, wherein said fungus is applied, along with a liquid carrier, directly to the fire ant nest.

11. A process, according to claim 8, wherein said fungus is applied, along with a powder, small particles, or granular carrier, directly to the fire ant nest.

12. A process, according to claim 8, wherein said fungus is applied as a bait, along with a powder, small particles, or granular carrier, directly to the nest and to the surrounding ground.

13. A process, according to claim 8, wherein said fungus is applied as a bait, along with a powder, small particles, or granular carrier together with an oil or any other attractant, directly to the nest and to the surrounding ground.

* * * * *